United States Patent [19]

Poulhes et al.

[11] Patent Number: 4,655,898

[45] Date of Patent: Apr. 7, 1987

[54] ELECTROPHORETIC FRACTIONATION APPARATUS

[75] Inventors: Marie-Andree Poulhes, Sainte-Genevieve; Jean-Pierre Lafaille, Saint-Orens; Jacques Pourrat, Toulouse; Victor Sanchez, Ramonville Saint-Agne, all of France

[73] Assignee: Rhone-Poulenc Recherches, Courbevoie, France

[21] Appl. No.: 880,949

[22] Filed: Jun. 26, 1986

Related U.S. Application Data

[63] Continuation of Ser. No. 762,846, Aug. 6, 1985, abandoned.

[30] Foreign Application Priority Data

Aug. 6, 1984 [FR] France ............................. 84 12579

[51] Int. Cl.⁴ ............................................. B01D 13/02
[52] U.S. Cl. ............................. 204/299 R; 204/180.1; 204/301
[58] Field of Search ................. 204/301, 299 R, 180.1

[56] References Cited

U.S. PATENT DOCUMENTS

| | | | |
|---|---|---|---|
| 2,801,962 | 8/1957 | Polson | 204/301 |
| 3,150,069 | 9/1964 | Nellen | 204/301 |
| 3,216,920 | 11/1965 | Nellen | 204/301 |
| 4,202,772 | 5/1980 | Goldstein | 204/301 |
| 4,375,401 | 3/1983 | Catsimpoolas | 204/301 |
| 4,437,967 | 3/1984 | Sanchez et al. | 204/301 |
| 4,561,953 | 12/1985 | Muralidhara et al. | 204/301 |
| 4,600,486 | 7/1986 | Oppitz | 204/299 R |

FOREIGN PATENT DOCUMENTS

2131859 11/1972 France .
505752 5/1939 United Kingdom .
505753 5/1939 United Kingdom .

*Primary Examiner*—Arthur P. Demers
*Attorney, Agent, or Firm*—Burns, Doane, Swecker & Mathis

[57] ABSTRACT

Electrophoretic fractionation apparatus well adopted for separating solutions containing diverse substances dissolved therein, e.g., such proteinaceous solutions as human plasma, is comprised of (i) a pair of opposed end plates, (ii) a pair of opposed electrodes, (iii) a pair of opposed frame members, (iv) at least two spaced membranes, said frame members, electrodes and membranes defining open electrode compartments between said end plates, and said frame members comprising inlet and outlet means for introducing and withdrawing an ionic solution into and from the central region of said electrode compartments, and (v) at least one fractionation plate disposed between said at least two membranes, and each said fractionation plate (v) comprising (1) at least one elongate slit extending through the thickness thereof and said slit defining, together with two of said spaced membranes, at least one solution fractionation chamber, (2) means for introducing solution to be fractionated into said at least one fractionation chamber, (3) means for withdrawing one fraction of fractionated solution from one end region of said fractionation chamber, and (4) means for withdrawing another fraction of fractionated solution from another end region of said fractionation chamber.

17 Claims, 5 Drawing Figures

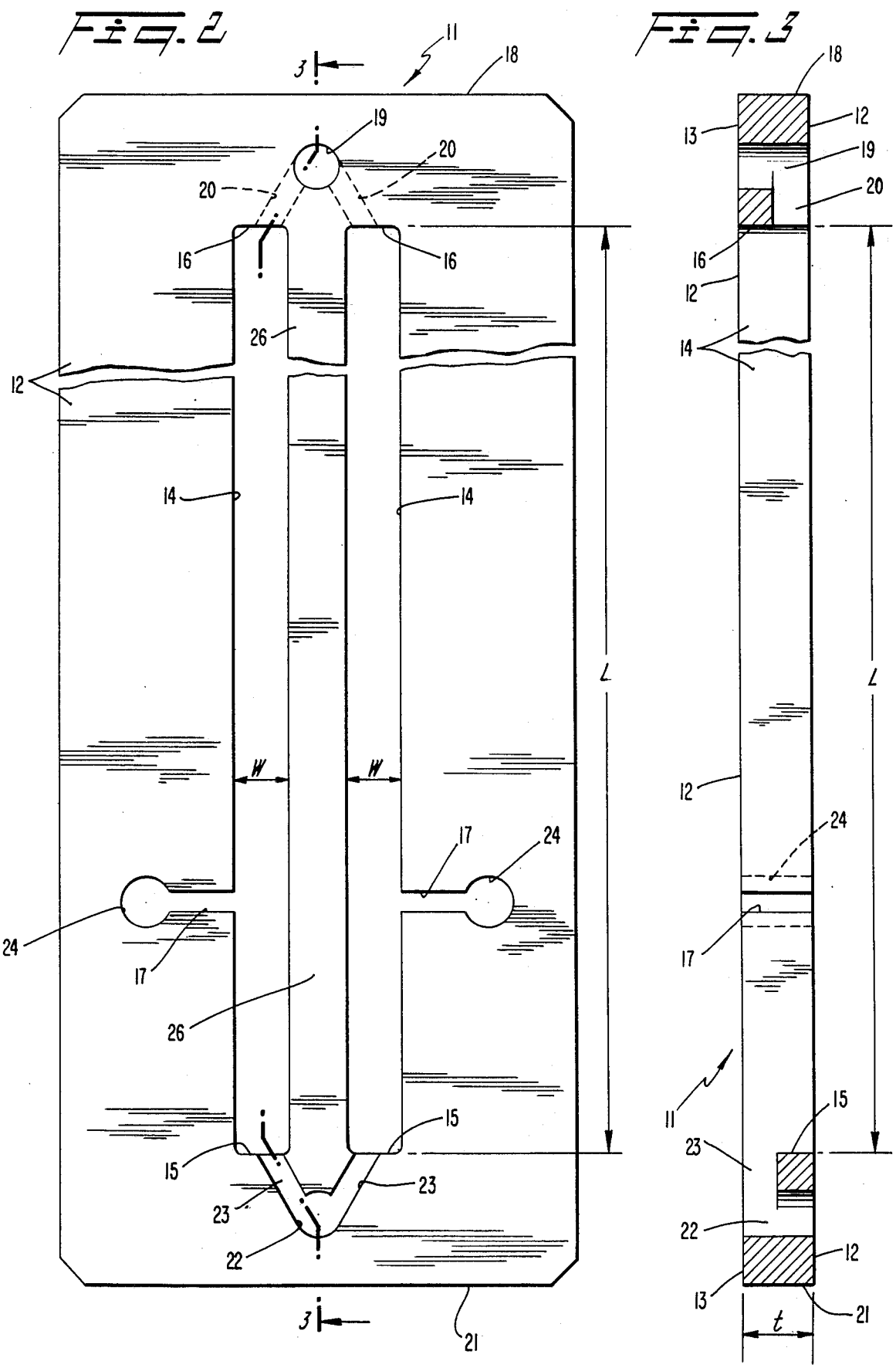

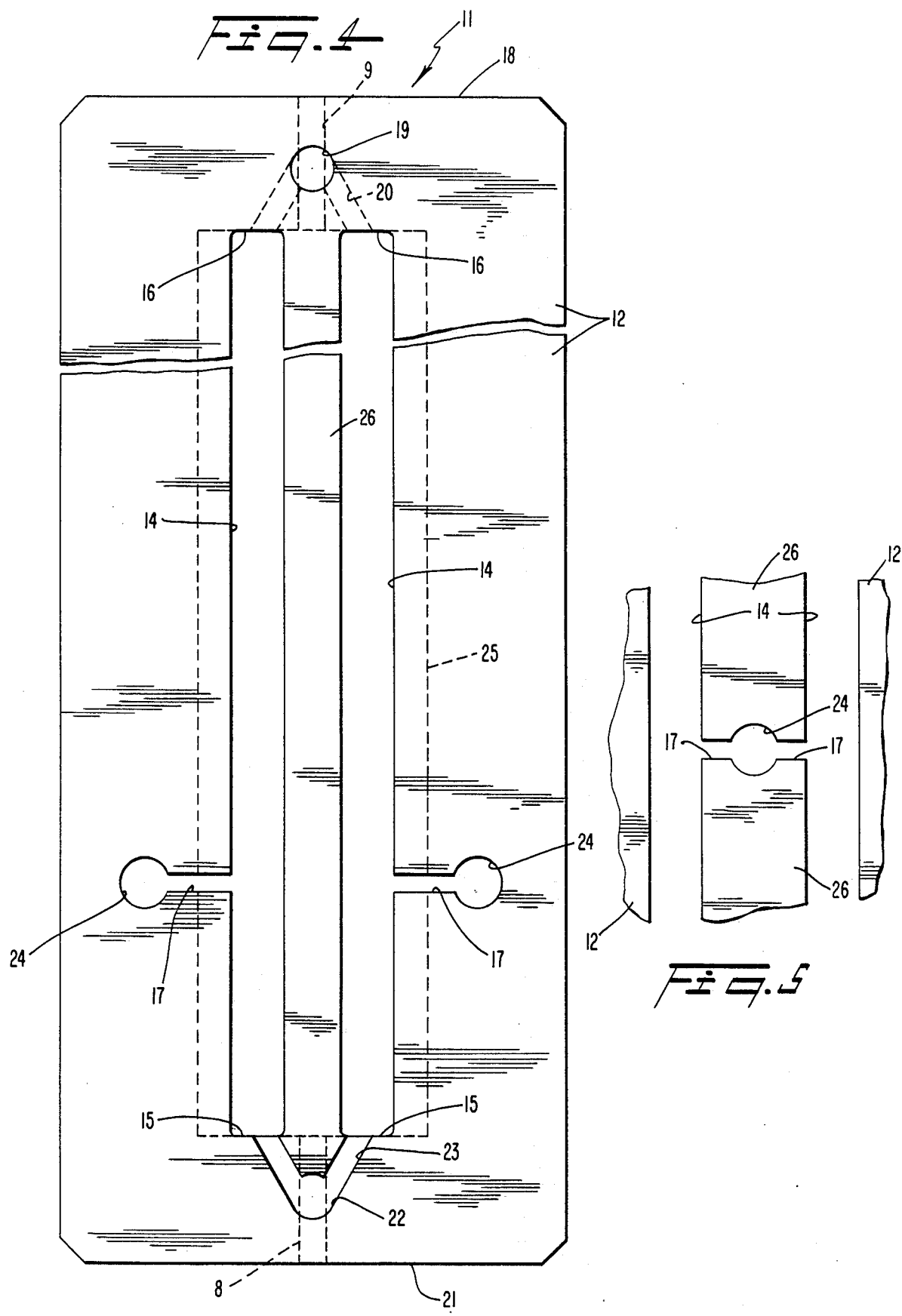

ELECTROPHORETIC FRACTIONATION APPARATUS

This application is a continuation of application Ser. No. 762,846 filed Aug. 6, 1985, now abandoned.

BACKGROUND OF THE INVENTION

1. Field of the Invention

The present invention relates to electrophoretic apparatus/process for fractionating a solution containing proteins, for the purpose of separating at least two groups of substances dissolved therein, and, more especially, relates to apparatus/process for fractionation by electrophoresis, under the influence of an electric field.

2. Description of the Prior Art

Electrophoresis is known to this art, e.g., for use in the laboratory to fractionate a solution and obtain liquid fractions enriched in substances present in the initial solution; the main advantage of this type of process is that it preserves the specific properties of the fractionated substances without denaturing them, and also that it entails little consumption of energy. Particularly compare, for example, French Pat. No. 2,131,859, U.S. Pat. Nos. 2,801,962, 2,878,178, 3,989,613 and British Pat. No. 936,805 as representative of a variety of electrophoresis processes/electrophoretic apparatus.

However, these prior art devices/processes only enable relatively mediocre yields to be obtained, very long operating times frequently being needed to obtain a given degree of fractionation.

Thus, in practice, the known devices mentioned above do not enable full use to be made of the advantages provided by electrophoresis processes (low energy consumption, lack of denaturation of the fractionated substances), due to the inherent defects in each of these devices, which preclude their use industrially. Furthermore, with most of the known fractionating devices, it is necessary to carry out a prior preparation of the initial solution, which has generally to be diluted and dialyzed to adjust its pH in order that efficient fractionation may be accomplished. These dialysis procedures are long and awkward, and are the source of bacterial contamination of the solutions.

A substantial improvement in these devices for fractionation by electrophoresis was achieved by the apparatus described in U.S. Pat. No. 4,437,967. However, this apparatus, as a result of the design of its fractionating chambers ($C_1$, $C_2$, etc.), each fabricated from two components (15 and 16), proved complicated to produce, and did not enable fractionations to be carried out leading, for example, to an enriched fraction containing more than 74% of gamma-globulins relative to the content of this component in the bovine serum introduced into the apparatus, unless feed rates less than or equal to 95 ml/h were used.

SUMMARY OF THE INVENTION

Accordingly, a major object of the present invention is the provision of improved electrophoresis apparatus/process having all of the advantages of the apparatus/process described in the aforenoted U.S. Pat. No. 4,437,967, but which is simpler to produce and which permits more effective fractionations at equal membrane areas; it is thus possible to collect a fraction containing, under the area conditions of Example 1 of said U.S. Pat. No. 4,437,967, 80% of the gamma-globulins introduced, such fraction, moreover, containing not more than 10% of the albumin introduced, whereas the other fraction contains 90% of the albumin introduced and only 20% of the gamma-globulins introduced, in a human plasma or bovine serum fractionation procedure with a feed rate on the order of 156 ml/h, equivalent to 1.6 times greater.

The apparatus of the present invention is very well suited for fractionating human plasma, in particular where it is desired to treat the plasma of a person having, for example, abnormalities in respect of his immunoglobulins, for example, his gamma-globulins, which it is desired to eliminate.

The device or apparatus of this invention makes it possible to continuously treat a patient whose blood has abnormalities, for example, abnormalities in respect of his immunoglobulins, and more especially his beta- or gamma-globulins, which it is sought to eliminate.

By way of examples of blood abnormalities which can be treated via a patient's plasma with the device according to the present invention, representative are diseases in which the plasma is withdrawn from a patient and replaced by the plasma of another person in good health. This process is designated more generally by the recognized term "plasma exchange".

Another advantage of the apparatus/process according to the present invention is that it enables a patient's plasma to be continuously treated without the need to reinject him with another plasma. With the apparatus according to the present invention, it is sufficient to reinject the patient with a replacement solution of suitable ionic composition, the volume and ionic composition of which correspond substantially to those of the fraction removed (while the patient is reinjected with the other fraction, since its proteins are not denatured).

Another advantage of the apparatus according to the present invention is that it enables a patient's plasma to be treated rapidly.

Another advantage of the apparatus according to the present invention derives from the fact that, in its specific adaptation of treating a patient's plasma, its "dead" volume (namely, the total volume to fill the fractionation compartments) is small, less than 400 $cm^3$ and preferably approximately 200 $cm^3$.

Another advantage of the apparatus according to the present invention also derives from the fact that, in the above-mentioned application of treating human plasma, it is possible to eliminate the so-called guard compartments designated $G_1$ and $G_2$ (page 6, line 10) in published European Patent Application No. 52,391 (corresponding to said U.S. Pat. No. 4,437,967) situated between the end fractionating chambers and the electrode compartments.

Briefly, the present invention features an apparatus for fractionation by electrophoresis, especially adopted for fractionating protein solutions, in particular those of human plasma, into two liquid fractions, said apparatus comprising:

(i) two end plates (1, 2), (ii) two electrodes (5, 6), (iii) two frames (3, 4) which define electrode compartments, situated between the two end plates (1, 2), each frame being adjacent to an end plate and a membrane (10) and incorporating means (8, 9) for the introduction and removal, into and from its hollow central portion (7), of an ionic solution which comes into contact with the electrode, (iv) at least one fractionation plate (11) situated between the two membranes (10) of the electrode compartments, said plate (11) of slight thickness incorporating at least one narrow slit (14) passing through the said plate and defining between the two membranes (10) a chamber for fractionating the protein solution to be treated, this slit (14), vertical or sloping in position in an apparatus when in operation, being connected to means (17) for introduction of the protein solution to be fractionated, the said means for introduction opening into the said slit (14) at least 1 cm from its base (15) and at most at half its length L measured from this base (15), the said slit (14) being connected towards its upper end (16) to means for removing the fraction of the fluid introduced which is directed upwardly, and being connected towards its lower end (15) to means for removing the fraction of fluid introduced which is directed downwardly, and (v) holding means which enable the plates (1, 2, 11), frames (3, 4) and membranes (10) to be maintained clamped together in a leakproof manner.

BRIEF DESCRIPTION OF THE DRAWINGS

FIG. 2 is a plan view, partially in cross-section, of one embodiment of a fractionation plate according to the invention;

FIG. 3 is a cross-sectional view taken along the line III—III of FIG. 2;

FIG. 4 is a plan view, partially in section, showing the relative positions of a fractionation plate and an electrode frame according to the invention; and FIG. 5 is a partial cross-sectional view of another embodiment of a fractionation plate according to the invention.

DETAILED DESCRIPTION OF THE INVENTION

Figure 1:
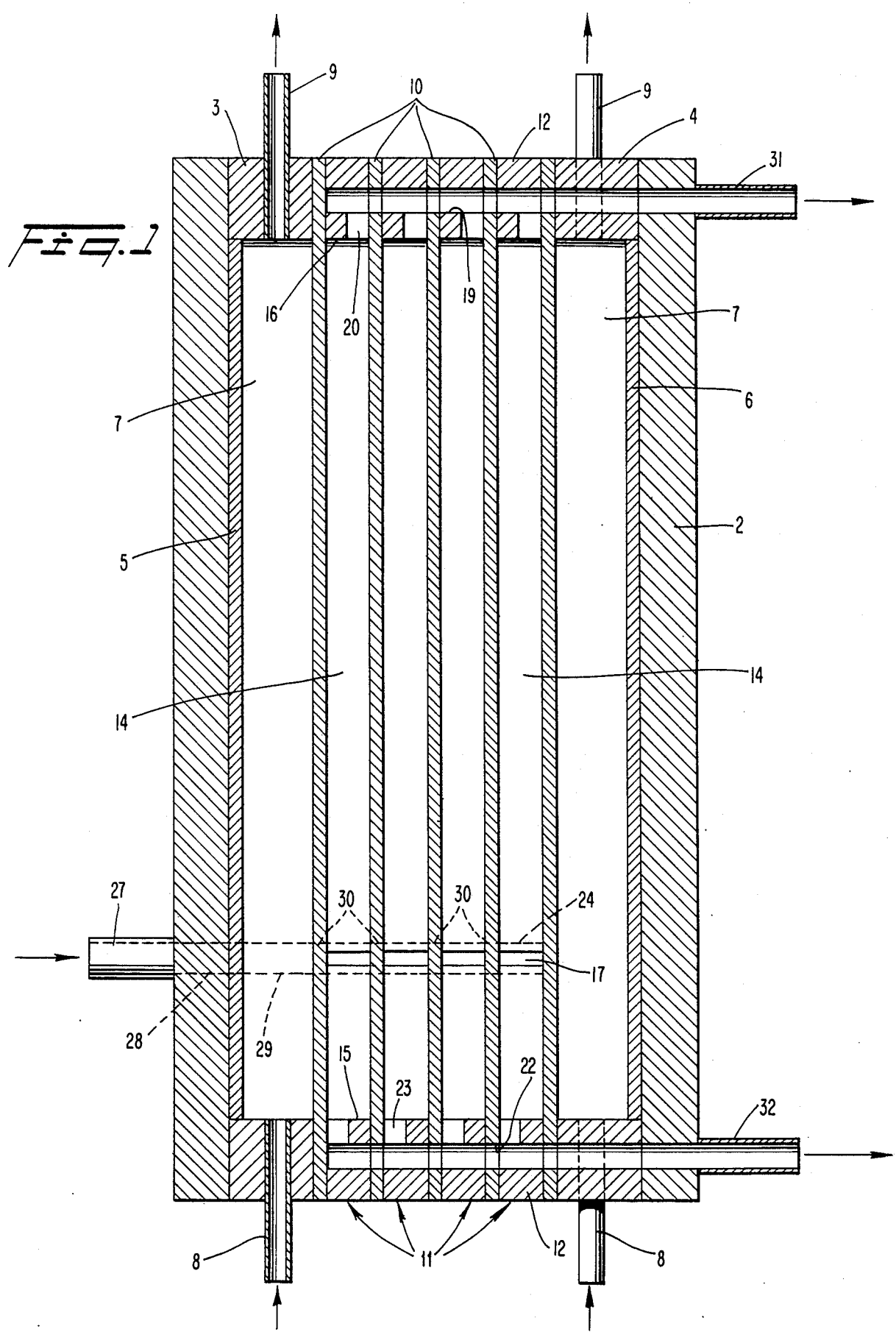
FIG. 1 is an overall cross-sectional view of one embodiment of the apparatus according to the present invention.

More particularly according to the present invention, the subject electrophoresis apparatus, which is admirably suited for the fractionation of human plasma, one embodiment of which is shown in FIGS. 1 to 4, comprises two end plates 1 and 2, each of which being adjacent to a frame, 3 and 4, respectively, and an electrode, 5 and 6, respectively, connected electrically to a direct current generator which is not shown. Each frame 3 and 4 comprises a hollow central portion 7 and tubulures 8 and 9 for introducing and removing an ionic solution which has to pass in contact with the electrodes 5 and 6. Each frame 3 and 4 is adjacent, via its face surface opposite that in contact with the end plate 1 or 2, to a membrane 10 and defines an electrode compartment inside of which the ionic solution passes; this electrode compartment, which can be designated by the reference number 7 corresponding to the hollow portion of the frame, is thus bounded by the inner wall of the end plate 1 or 2 and by a membrane 10. Between these two frames 3 and 4, situated between the end plates 1 and 2, fractionation plates 11 are disposed, the number of which is four in the apparatus shown in FIG. 1. This apparatus according to the present invention can of course contain fewer or more plates 11. As can be seen in FIG. 1, each plate 11 is contiguous, at each of its principal face surfaces 12 and 13, a membrane 10.

Each plate 11, as shown in FIGS. 2 and 3, comprises two openings or slits 14 which extend completely through the thickness of said plate and define, between a set of two membranes 10, two chambers for fractionating the protein solution to be separated. Each slit 14 is narrow, i.e., its width w is small relative to its length L, the ratio w/L being less than 1:5, and preferably less than 1:15. Each fractionation chamber is thus elongated in shape.

In an apparatus in operation the longitudinal axis of each slit 14 is arranged vertically relative to the ground or is sloping (as is the case with each face surface 12 and 13 of the plate 11) at a certain angle relative to the ground, i.e., each slit, over its length L, has a base or bottom 15 corresponding to its lower end relative to the ground, and a top 16 corresponding to its upper end relative to the ground. Each slit is connected to means 17 for introducing, into the latter, the protein solution to be fractionated, the said means 17 opening into the said slit at a point situated at least 1 cm from its base 15 and at most at half its length L measured from the base 15 of the slit 14. The means 17 for introducing the solution to be fractionated preferably open into each slit 14 at a point situated at least 2 cm above its base 15 and at most at one-quarter of the length L of the slit. The means 17 for introduction are hence closer to the base 15 of each slit than to its top 16.

The means 17 for introducing the fluid to be fractionated inside each slit 14 comprise, for example, as is shown, a narrow passage 17 passing through the plate, said passage 17 being connected to an aperture 24 also passing through the plate. The passage 17 is preferably narrower than the width of the slit 14 and than the diameter of the aperture 24, which is advantageously circular. Although in the embodiment of the fractionation plate 11 shown in FIGS. 2 and 3 there are two apertures 24, it is naturally possible to provide only one aperture 24 situated between the two slits 14, this aperture 24 then being on the strip 26 through which it passes, said strip 26 being between the two slits 14. In this case, the aperture 24 situated on the strip 26 is connected to each slit 14 by two diametrically opposed passages 17 on the circumference of this aperture 24, each passage 17 opening into one slit 14. In this embodiment, shown partially in FIG. 5, it is advantageous that the frame 3 should contain a strip corresponding to that (26) of each fractionation plate 11 and that a passage 29 (further discussed hereinbelow) in alignment with the aperture 24 should be provided in this strip in the frame 3.

Each fractionation plate 11 further contains:

(a) towards its upper end 18, means for removing the fraction of the solution introduced at 17 which is transported towards the top of the plate, these means comprising, for example, a hole 19 extending through the plate and channels 20 or grooves connecting each slit 14 to this hole, and (b) towards its lower end 21, means for removing the fraction of the solution introduced at 17 and which is transported towards the bottom or base of the plate, these means comprising, for example, a hole 22 extending through the plate 11 and channels 23 or grooves connecting or communicating each slit 14 to this hole 22.

It is advantageous, for better fractionation of the solution containing the proteins introduced into the apparatus, that the means for removal 23 of the fraction which is conveyed towards the bottom of each slit 14 is on the side of migration of the charged proteins under the influence of the electric field, namely, towards the face surface of each plate 11 which is closer to the electrode which serves the function of anode, while the means for removal 20 of the fraction conveyed towards the top of each slit 14 are closer to or on the other face surface of each plate. With the apparatus shown in FIG. 1, the electrode 5 is thus advantageously the anode, in the fractionation of human plasma.

In the apparatus as described above, the membranes 10 only have passages or orifices therethrough which correspond with the holes 19 and 22 and with the apertures 24 extending through the plates 11 and in communication with the means 17 for introducing the solution to be fractionated into the slits 14.

To ensure absence of leakage, the two fractionation plates 11 adjacent to the frames 3 and 4 of the apparatus described above have their channels 20 and 23 on the same face surface of each plate. Thus, the plate 11 adjacent to the frame 3 has its channels 20 and 23 both on the face surface of the plate not adjacent to the frame in question, while the plate 11 adjacent to the frame 4 has its channels 20 and 23 both on the face surface of the plate not adjacent to the frame in question. Also to ensure freedom from leakage, the two plates 11 adjacent to the frames 3 and 4 have passages 17 which do not extend through the plates, and for this reason the face surfaces (close to the frames 3 and 4) of the plates 11 are flat and are not traversed by the passages 17, which thus occupy only part of the thickness of these plates. These details have not been shown in FIG. 1 for reasons of simplification.

As regards the frames 3 and 4, as is seen in FIG. 1 and FIG. 4, in which the periphery of the central hollow portion 7 is shown by a broken line 25 (the frame 3 being imagined to be behind a fractionation plate 11), it is sufficient that the central hollow portion 7, the size of which corresponds substantially to that of the electrode 5 or 6, should be equal to or slightly larger than the maximum distance between the furthest removed portion of the slits 14.

The apparatus as described above contains holding means (not shown) which enable the different frames, membranes and plates defined above to be maintained clamped together. These holding means can be, for example, a system of screw clamping, between two plates, such as that shown in perspective in FIG. 1 of the aforenoted U.S. Pat. No. 4,437,967. The holding device can advantageously consist of side plates which clamp the frames 3 and 4, membranes 10 and fractionation plates 11 between the end plates 1 and 2. Such side plates are shown, for example, in French Pat. Nos. 2,114,731 (in FIG. 8) and 2,482,055 (in FIG. 8, reference 28), and European Pat. No. 23,188.

To use the apparatus described above, the procedure is as follows, particular reference being made to FIG. 1 which is an overall sectional view according to the broken line III—III of the plate in FIG. 2:

(i) the ionic solution is passed through each electrode compartment 7, by means not shown, the solution entering each chamber through the tubulure 8 and exiting same through the tubulure 9, (ii) each electrode 5 and 6 is set at the desired electrical voltage, (iii) the protein solution to be fractionated is continuously introduced into the apparatus through the two tubulures 27, only one of which is shown in FIG. 1. Each tubulure 27 is in alignment or registration with the apertures 24 of the fractionation plates 11 and the protein solution reaches these apertures 24 in the fractionation plates 11 after passing through corresponding apertures: 28 in the end plate 1, 29 in the frame 3, and 30 in the membranes 10. The protein solution to be fractionated is then conveyed into the passages 17 in the fractionation plates 11, and then simultaneously enters the slits 14, namely, the fractionation chambers defined between two successive membranes 10.

The protein solution then continuously divides into two fractions:

(1) an ascending fraction, enriched in proteins of a certain type, this fraction rising towards the top 16 of each slit 14, passing through the channels 20 into the holes 19 and then reaching the tubulure 31 after passing through the membranes 10 by the holes or conduits therein adjacent to the holes or conduits 19.

(2) a descending fraction, depleted in proteins of the type of which the ascending fraction is enriched, this fraction travelling towards the bottom 15 of each slit 14, passing through the channels 23 into the holes or conduits 22 and exiting the apparatus through the tubulure 22 after passing through the membranes 10 by the holes or conduits therein in alignment or registration with the holes or conduits 22.

More generally, the descending fraction is enriched in proteins charged under the influence of the electric field.

In FIG. 1, the protein solution to be fractionated continuously entering the apparatus is shown schematically by the full single-headed arrow, the ascending fraction continuously exiting the apparatus is shown by a full double-headed arrow, while the descending fraction continuously exiting the apparatus is shown schematically by a full three-headed arrow.

The apparatus according to the present invention is subject to many variations. It is possible, for example, for an end plate and the adjacent frame to form, in reality, only a single part. The fractionation plates 11 can incorporate more or less than two slits 14; by way of example, each plate 11 can have four slits 14.

In another embodiment of the invention, each fractionation plate 11, instead of having channels 20 on its face surface 12 and channels 23 on its opposite face surface 13, can contain ducts internal to the plate 11 in question, the said ducts connecting each end 15 or 16 of each slit 14 to the holes or conduits 19 or 22. For better fractionation, the said above-mentioned internal ducts, which are within the thickness t of each plate 11 are preferably closer, towards the lower end 15 of each slit, to the face of each plate which is closest to the electrode performing the role of anode. The internal ducts close to the upper end 16 of each slit 14 are close to the face of the plate opposed to that closest to the anode. Moreover, the passages 17 which extend through the plates 11 and connect the apertures 24 to the slits 14 can be within each plate 11. By the two embodiments thereof, the two fractionation plates 11 adjacent to the frames 3 and 4 can be identical to the other plates 11 of the apparatus.

As regards membranes which can be used in the apparatus according to the present invention, semi-permeable membranes such as those used in reverse osmosis apparatuses have proved to be very suitable. Such membranes are widely available on the market. For example, representative are cellophane semi-permeable membranes which are fabricated from regenerated cellulose. Membranes such as these, and which have very small amounts of pendant ionic groups, for example, sulfonic acid groups $SO_3^-$, are also suitable.

The apparatus according to the present invention can have fractionation plates 11 of sizes which vary widely depending upon the application contemplated. This apparatus can of course be used for the industrial fractionation of protein solutions. It is particularly well suited for the fractionation of human plasma. With an apparatus according to the present invention it has thus been possible to remove, in two hours, 50% and even 70% of the gamma-globulins of the plasma of patients suffering from IgG myeloma (continuously treating the patients).

The plates 11 can be made of any dielectric material which is neutral towards the initial solutions to be treated, for example of polymethylmethacrylate or "PLEXIGLAS".

The electric field between two successive membranes 10 generally ranges from 250 to 400 V/m.

The width w of the slits 14 generally ranges from 0.5 to 2 cm, and preferably from 0.75 to 1.25 cm for membranes 10 which are not reinforced, for example, by an internal fabric.

For the continuous fractionation of human plasma with cellophane membranes, the thickness of the fractionation plates 11 has proved to advantageously range from 1.3 to 1.7 mm.

For a rate of inflow of human plasma to be fractionated on the order of 25 to 40 ml/min., it was found that it was especially advantageous to provide a potential difference between electrodes of 30 to 40 volts, the current intensity passing through the chambers ranging from 1.6 to 2 amperes.

As regards the electrodes, these must not introduce contaminant ions into the solution to be fractionated. By way of examples, they can be of platinum (in grid form) or of carbon or graphite (in plate form).

In order to further illustrate the present invention and the advantages thereof, the following specific examples are given, it being understood that same are intended only as illustrative and in nowise limitative.

EXAMPLE 1

Human plasma in a container was fractionated, by introducing this plasma into an apparatus such as that described above in FIGS. 1 to 4, containing 15 plates 11 according to FIG. 2, namely, with two slits 14, each of width w 1 cm and length L 24 cm, the plate thickness being 0.15 cm. Each slit was disposed vertically relative to ground.

The dead volume of the apparatus was 108 ml.

The electrodes 5 and 6 were platinum grids, the electrode 5 close to the tubulures 27 being the anode.

The membranes 10 were cellophane, reference 600 N.

The frame thickness (3, 4) was 1 cm.

The potential difference (p.d.) between electrodes was 30 volts.

The current intensity passing through the chambers was 1.6 amperes.

The height of the passages 17 in each plate was at 1/6 of the length L of the slits 14, namely, at 4 cm from the bottom 15 of each slit 14.

The ionic solution passing through the electrode compartments 7 was a 9:1000 strength NaCl solution and its flow rate was 3.5 liters per hour (1/h).

The human plasma solution passed through the apparatus at an inflow rate (at 27) of 900 ml/h. The flow rate of the fraction exiting the tubulure 31, namely, the ascending fraction or high fraction, was 450 ml/h; this flow rate will be designated fH.

The flow rate of the fraction exiting the tubulure 32, namely, the descending fraction or bottom fraction, was also 450 ml/h; this flow rate will be designated fB.

As can be seen:

$$R = \frac{fH}{fB} = 1$$

The two fractions collected at 31 and 32 were each collected in a separate container, and assays were carried out on each fraction obtained.

Under the operating conditions defined above, and with the apparatus described, the following results were obtained (regardless of the time interval):

$$(I) = \frac{\text{amount of gamma-globulins collected at 31}}{\text{amount of gamma-globulins introduced at 27}} \times 100 = 55\%$$

$$(II) = \frac{\text{amount of albumin collected at 32}}{\text{amount of albumin introduced at 27}} \times 100 = 92\%$$

Thus, in the high fraction, there was not more than 8% of the albumin introduced into the apparatus, while in the bottom fraction there was not more than 45% of the gamma-globulins introduced into the apparatus.

EXAMPLE 2

The procedure was performed under the same conditions as those of Example 1, except as regards the inflow rate of the plasma into the apparatus, which was 300 ml/h, and as regards R, which was equal to 3.

Thus, fH=225 ml/h and fB=75 ml/h.

The results obtained were:

I=80%

II=92%

I and II have the same significance as in Example 1.

EXAMPLE 3

The procedure was performed under the same conditions as those of Example 2, but with plates of thickness t 0.2 cm. The dead volume of the apparatus was then 144 ml.

The results were:

I=80%

II=90%

This apparatus was less advantageous, patient-wise, than the apparatus according to Example 2, which had a dead volume of only 108 ml.

EXAMPLE 4

The procedure was performed under the conditions of Example 1 with the same apparatus, except as regards the height of introduction of the fluid to be fractionated into the slits 14.

A trial was carried out with introduction at the points ⅛L, ⅓L and ½L, that is to say, at 3 cm, 8 cm and 12 cm from the bottom 15 of each slit 14.

The results obtained are reported below:

| Introduction | ⅛ L | ⅓ L | ½ L |
| --- | --- | --- | --- |
| I | 55% | 55% | 55% |

| -continued | | | |
|---|---|---|---|
| Introduction | ⅓ L | ⅓ L | ⅓ L |
| II | 93% | 80% | 75% |

EXAMPLE 5

A continuous trial was carried out, for two hours, on a patient, in a comatose state at the beginning of the session, suffering from IgG myeloma. The plasma of this patient, at the beginning of the session, contained 29 g/l of gamma-globulins and 32 g/l of albumin.

The apparatus used was the same as that of Example 1, except as regards the number of fractionation plates 11, which had been increased to 30.

The operating conditions were the same as those of Example 1 (R was equal to 1), except as regards the fact that the plasma was withdrawn continuously from the patient's blood and that the plasma entered the apparatus at 27 at a flow rate of 30 ml/min (milliliters per minute).

Thus, the patient's blood was drawn off continuously, into an extracorporeal circuit, his blood was passed over a membrane-containing separator of known type, to extract a portion of his plasma therefrom, which passed through the membrane (recovery of this plasma took place at a flow rate of 30 ml/min), while the fraction of the blood not passing through the membrane was returned continuously to the patient through a blood return line (this latter fraction containing the formed elements of the blood and the portion of the plasma which had not passed through the membrane).

Thus, the patient's plasma passing continuously through the membrane of the separation apparatus was introduced continuously into the apparatus according to the present invention through the tubulures 27.

The fraction of the patient's plasma collected at the high outflow 31 of the apparatus was recovered in a container, while the fraction exiting the low tubulure 32 was continuously conveyed back to the patient through the blood return line, while continuously adding into this line for returning the fraction exiting through the tubulure 32 a replacement solution (equivalent to 1,800 ml in two hours, since R=1) prepared by mixing:

(i) 1,500 ml of NaCl, 0.15 mole/liter
(ii) 750 ml of water
(iii) 60 ml of NaHCO$_3$, 0.1 mole/liter
(iv) 9 ml of KCl, 10% by weight
(v) 15 ml of calcium gluconate, 10% by weight.

The patient awoke during the session.

Upon completion of the session, the amount of gamma-globulins recovered through the high tubulure 31 of the apparatus represented 55% of the amount of gamma-globulins present in the patient's plasma at the beginning of the session. The amount of albumin recovered in the same fraction (exiting at the top of the apparatus) represented 20% of the albumin present in the patient's plasma at the beginning of the session.

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. Electrophoretic fractionation apparatus adopted for separating solutions containing diverse substances dissolved therein, comprising (i) a pair of opposed end plates, (ii) a pair of opposed electrodes, (iii) a pair of opposed frame members, (iv) at least two spaced membranes, said frame members, electrodes and membranes defining open electrode compartments between said end plates, and said frame members comprising inlet and outlet means for introducing and withdrawing an ionic solution into and from the central region of said electrode compartments, and (iv) at least one fractionation plate disposed between said at least two membranes, the plate having a greater length than width, and each said fractionation plate (v) comprising (1) at least one elongate slit extending along the length of the plate and through the thickness thereof and said slit defining, together with two of said spaced membranes, at least one solution fractionation chamber, (2) means for introducing solution to be fractionated into said at least one fractionation chamber, (3) means for withdrawing one fraction of fractionated solution from one end region of said fractionation chamber, and (4) means for withdrawing another fraction of fractionated solution from another end region of said fractionation chamber.

2. The apparatus as defined by claim 1, said at least one elongate slit (1) being generally vertical.

3. The apparatus as defined by claim 1, said at least one elongate slit (1) being angled with respect to the longitudinal axis of said at least one fractionation plate.

4. The apparatus as defined by claim 1, said means (2) opening into said slit (1) at a distance no more than half the length of said slit, measured from the base thereof.

5. The apparatus as defined by claim 4, said means (2) opening into said slit (1) at least 1 cm from the base thereof.

6. The apparatus as defined by claim 5, said means (2) opening into said slit (1) at least 2 cm from the base thereof.

7. The apparatus as defined by claim 6, said means (2) opening into said slit (1) at a distance no more than one-quarter the length of said slit, measured from the base thereof.

8. The apparatus as defined by claim 1, further comprising means for the leakproof clamping thereof.

9. The apparatus as defined by claim 1, comprising a plurality of fractionation plates (v), each such fractionation plate being sandwiched between two membranes (iv).

10. The apparatus as defined by claim 1, said means (2) comprising an aperture extending through the thickness of the fractionation plate, and said aperture communicating with a conduit into said slit (1).

11. The apparatus as defined by claim 10, each respective membrane comprising a hole in registration with said aperture.

12. The apparatus as defined by claim 1, said means (4) being at the base of said slit (1) and more proximate the anode facing surface of the fractionation plate, and said means (3) being at the upper end region of said slit (1) and more proximate the cathode facing surface of the fractionation plate.

13. The apparatus as defined by claim 12, said means (4) comprising a channel or duct communicating with the base of said slit (1) and with a hole extending through the thickness of the fractionation plate.

14. The apparatus as defined by claim 13, said means (3) comprising a channel or duct communicating with the upper end region of said slit (1) and with a hole extending through the thickness of the fractionation plate.

15. The apparatus as defined by claim 14, each membrane contiguous each fractionation plate comprising holes extending through the thickness thereof in registration with the holes through the fractionation plate.

16. The apparatus as defined by claim 1, the thickness of each fractionation plate ranging from 1.3 to 1.7 mm.

17. The apparatus as defined by claim 16, each said slit (1) having a width to length ratio of less than 1:5.

* * * * *